United States Patent [19]

Middleton

[11] 4,215,044

[45] Jul. 29, 1980

[54] SYNTHESIS OF α-FLUOROCARBONYL COMPOUNDS

[75] Inventor: William J. Middleton, Chadds Ford, Pa.

[73] Assignee: E. I. Du Pont de Nemours and Company, Wilmington, Del.

[21] Appl. No.: 32,347

[22] Filed: Apr. 23, 1979

[51] Int. Cl.$^2$ .......................................... C07D 243/24
[52] U.S. Cl. ...................... 260/239.3 D; 260/538 R; 560/62; 560/105; 560/227; 562/471; 562/472; 562/496; 260/239.3 R; 260/343.5; 260/343.6; 260/397.4; 260/326 A; 546/335; 549/70; 549/79; 562/466; 562/510; 560/192; 560/145; 568/303; 568/316; 568/325; 568/326; 568/335; 568/348; 568/376; 568/393; 568/419; 568/425; 568/433; 568/458; 568/495
[58] Field of Search .................... 260/239.3 D, 586 R, 260/586 G, 599, 593 H, 601 H, 590 D, 590 R, 592, 558 R; 560/62, 105, 227; 562/472, 471, 496

[56] References Cited

U.S. PATENT DOCUMENTS 4,030,994   6/1977   Kollonitsch ................. 204/158 HE

OTHER PUBLICATIONS

Reuss et al. "J. Org. Chem." vol. 39, No. 12, (1974) pp. 1785–1787.
House et al. "J. Org. Chem." vol. 34, No. 8, (1969) pp. 2324–2336.
Cady "Proc. Chem. Soc." (1960) pp. 133–138.
Sheppard "Organic Fluorine Chemistry" (Benjamin)(1969) pp. 124–127, 220–221, 230–231, 480–481.
Barton et al. "Chem. Comm." (1968), pp. 804–808.
Hoffman "Chemical Reviews" (1964) vol. 64, pp. 91–98.
Prager et al. "J. Am. Chem. Soc." vol. 87, No. 2, (1965) pp. 230–238.
Thompson "J. Am. Chem. Soc." vol. 89, No. 8, (1967) pp. 1811–1813.

Primary Examiner—John M. Ford
Assistant Examiner—Robert T. Bond

[57] ABSTRACT

Process for preparing an organic compound of the formula $R^2R^2CFC(O)R^3$, which process comprises contacting and reacting in a reaction mixture which includes an inert solvent, at a temperature of −40° C. to −100° C., ROF and

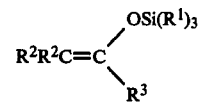

R is polyfluoroperhaloalkyl of 1–6 carbon atoms or $FOCF_2$;
$R^1$ is hydrocarbyl of 1–6 carbon atoms;
each $R^2$ is selected from H, alkyl of 1–17 carbon atoms, cycloalkyl of 3–6 carbon atoms, aryl, heteroaryl and such alkyl, cycloalkyl, aryl and heteroaryl substituted by halogen or alkoxy of 1–6 carbon atoms;
$R^3$ is selected from H, alkyl and haloalkyl of 1–16 carbon atoms, cycloalkyl of 3–10 carbon atoms, aryl and haloaryl, $OSi(R^1)_3$, OH, $NH_2$, alkoxy of 1–6 carbon atoms, aryloxy, $NHR^1$ and $NR^1_2$ wherein $R^1$ is alkyl of 1–6 carbon atoms, N-arylamino and nitrogen or sulfur heterocyclic of 4–5 carbon atoms;
$R^3$ and one $R^2$ taken together is a diradical which with the C=C group is carbocyclic, heterocyclic or haloheterocyclic, and recovering from the reaction mixture the compound of the formula $R^2R^2CFC(O)R^3$.

14 Claims, No Drawings

SYNTHESIS OF α-FLUOROCARBONYL COMPOUNDS

DESCRIPTION

1. Technical Field

This invention relates to the synthesis of organic compounds having an α-fluorocarbonyl moiety.

2. Background Information

Reuss et al., J. Org. Chem., 39, 1785 (1974) disclose the preparation of α-chloro- and α-bromo-substituted aldehydes and ketones. A non-α-halogenated aldehyde or ketone having an enolizable hydrogen atom alpha to the carbonyl group is converted to a trimethylsilyl enol ether, by known techniques, for example, as disclosed by House et al., J. Org. Chem., 34, 2324 (1969), and the enol ether is treated with either chlorine or bromine to obtain the desired α-halo-substituted aldehyde or ketone.

Trifluoromethyl hypofluorite is known in the art as an oxidizing agent and a fluorinating agent. Such use is disclosed, for example, by Cady, Proc. Chem. Soc., 1960, 133 and by Sheppard et al., "Organic Fluorine Chemistry," W. A. Benjamin, Inc., New York, 1969, in the treatise "Frontiers In Chemistry" edited by Breslow et al. The disclosures in these publications include addition of trifluoromethyl hypofluorite to olefinic double bonds. The addition of trifluoromethyl hypofluorite to activated olefins, in the field of cholestanone, and aromatic rings is discussed by Barton et al. in Chem. Commun., 1968, 804 and 806, respectively. Additional reactions of trifluoromethyl hypofluorite are disclosed by Hoffman, Chem. Rev., 64, 91 (1964).

The preparation of various polyfluoroperhaloalkyl hypofluorites, such as 1- and 2-fluoroxyperfluoropropane, 2-fluoroxyperfluoro-2-methylpropane, 1-nitro- and 1-chloro-2-fluoroxyperfluoroethane, fluoroxyperfluoroethane and bis(fluoroxy)perfluoromethane, is described by Prager and Thompson, J. Am. Chem. Soc. 87, 230 (1965) and by Thompson, ibid., 89, 1811 (1967).

It is an object of this invention to provide a simple process for synthesizing organic compounds having an α-fluorocarbonyl moiety. Another object is to provide a controllable process for preparing such compounds using a readily available trialkylsilyl enol ether and a readily available hypofluorite as starting materials. A further object is to provide a process wherein the by-products of the reaction being carried out are readily removable gaseous materials. Other objects will become apparent hereinafter.

Disclosure of Invention

For further comprehension of the invention, and of the objects and advantages thereof, reference may be made to the following description and to the appended claims in which the various novel features of the invention are more particularly set forth.

The present invention resides in a process for synthesizing organic compounds having an α-fluorocarbonyl moiety. More specifically, the invention resides in the process of contacting and reacting in a reaction mixture which includes an inert solvent, at a temperature of $-40°$ C. to $-100°$ C., ROF and

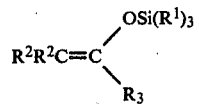

wherein

R is polyfluoroperhaloalkyl of 1-6 carbon atoms (preferably perfluoroalkyl of 1-4 carbon atoms, more preferably $CF_3$) or $FOCF_2$;

$R^1$ is hydrocarbyl of 1-6 carbon atoms (preferably alkyl of 1-4 carbon atoms, more preferably methyl);

each $R^2$ is selected from H, alkyl of 1-17 carbon atoms, cycloalkyl of 3-6 carbon atoms, aryl (preferably of 6-10 carbon atoms), heteroaryl (preferably of 6-10 carbon atoms) and such alkyl, cycloalkyl, aryl and heteroaryl substituted by halogen or alkoxy of 1-6 carbon atoms;

$R^3$ is selected from H, alkyl and haloalkyl of 1-16 carbon atoms, cycloalkyl of 3-10 carbon atoms, aryl and haloaryl (preferably of 6-10 carbon atoms), $OSi(R^1)_3$, OH, $NH_2$, alkoxy of 1-6 carbon atoms, aryloxy (preferably of 6-10 carbon atoms), $NHR^1$ and $NR^1_2$ wherein $R^1$ is alkyl of 1-6 carbon atoms, N-arylamino (preferably of 6-10 carbon atoms) and nitrogen or sulfur heterocyclic of 4-5 carbon atoms;

$R^3$ and one $R^2$ taken together is a diradical which with the C=C group is carbocyclic, heterocyclic or haloheterocyclic (each preferably of 5-16 carbon atoms), and recovering from the reaction mixture the organic compound of the formula $R^2R^2CFC(O)R^3$.

Using trifluoromethyl hypofluorite and a trimethylsilyl enol ether as reactants, the reaction carried out by means of the process of this invention may be represented as follows:

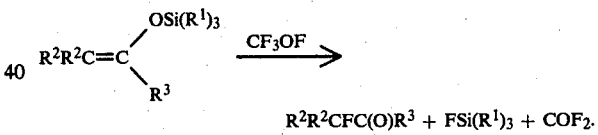

$$R^2R^2CFC(O)R^3 + FSi(R^1)_3 + COF_2.$$

The by-products shown are gaseous materials which can be separated from the desired product readily.

The process of the invention provides a means for converting a carbonyl compound into its corresponding α-fluoro derivative, via the intermediate trihydrocarbylsilyl enol ether which can be prepared by standard procedures wherein the carbonyl compound, in its enol form or as an alkali metal salt of the enol form, is reacted with a readily available halotrihydrocarbylsilane, such as chlorotriethyl-, chlorotributyl-, chlorotriphenyl- or chlorobutyldimethylsilane.

Examples of hypofluorites that can be used in the invention process include $CF_3OF$, $CF_3CF_2OF$, $(CF_3)_2CFOF$ and $CF_2(OF)_2$. The preferred hypofluorite is $CF_3OF$.

Carbonyl group-containing compounds that can be fluorinated through use of the process of this invention are those that possess at least one enolizable hydrogen atom on the carbon atom which is alpha to the carbonyl group. Included are aldehydes, ketones, esters, lactones, lactams, amides, carboxylic acids and anhydrides.

When a carboxylic acid is employed as the carbonyl group-containing compound, the halotrihydrocarbylsilane reacts with the hydroxy group of the acid as well as with the enol form of the carbonyl group. The invention process involving an acid may be represented as proceeding through the bis-(trihydrocarbylsiloxy) intermediate as follows:

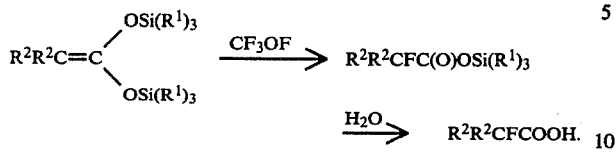

When a hydroxy or primary or secondary amino group is present in the carbonyl group-containing compound, the halotrihydrocarbylsilane reacts with the active hydrogen atom of such group, generally before additional silane reacts with the enol form of the carbonyl group. Hence, additional halotrihydrocarbylsilane must be used when the carbonyl compound contains such a substituent. After reaction of the intermediate with the hypofluorite, followed by hydrolysis, the original hydroxy or amino group is regenerated.

When an amide is used as the carbonyl group-containing compound, it is preferred to use a higher silane, such as tert-butyldimethylchlorosilane, to form the siloxy intermediate, for example, as described by Woodbury, J. Org. Chem. 43, 881 (1978).

The fluorination of the trialkylsilyl enol ether with hypofluorite can be carried out by dissolving the ether in a suitable solvent which is inert to the hypofluorite, cooling the resultant solution to a temperature of $-40°$ C. to $-100°$ C., and then passing the hypofluorite into the solution. Particularly useful as solvent are the halogenated hydrocarbons, such as the chlorofluorohydrocarbons, for example, $CCl_3F$, $CF_2Cl_2$, $CHF_2Cl$, $CClF_2CClF_2$ or $CCl_2FCClF_2$, and the chlorohydrocarbons, for example, $CCl_4$, $CHCl_3$ or $CH_2Cl_2$. The molar ratio of the reactants is not critical, although optimum yields generally are obtained when approximately stoichiometric amounts of the silyl enol ether and the hypofluorite are used. The reaction is most conveniently carried out at atmospheric pressure, but a higher or lower pressure can be used, if desired. The α-fluorocarbonyl compound that is formed can be isolated from the reaction mixture, for example, by evaporating off the solvent; it can be purified, if desired, by conventional means, such as by distillation or recrystallization.

EXAMPLE 1

Fluorination of 4-Fluoroacetophenone

A mixture of 34.56 g (0.25 mol) of 4-fluoroacetophenone, 32.6 g (0.3 mol) of chlorotrimethylsilane, 60.6 g (0.6 mol) of triethylamine and 100 ml of dimethylformamide was refluxed overnight, cooled, and diluted with 200 ml of pentane. This mixture was washed successively three times with 300 ml of cold 5% aqueous sodium bicarbonate, with cold 1.5 N hydrochloric acid, and with 5% aqueous sodium bicarbonate, dried and distilled to give 19.44 g of 1-(4-fluorophenyl)vinyloxytrimethylsilane as a colorless liquid: bp 55°–57° C. (0.12 mm); $^{19}F$ NMR (CFCl$_3$) δ−114.1 ppm (m); $^1H$ NMR (CFCl$_3$) δ 0.25 ppm (s, 9H), 4.35 ppm (d,J=1.5 Hz, 1H), 4.77 ppm (d,J=1.5 Hz, 1H), 6.9 ppm (m, 2H) and 7.5 ppm (m, 2H). Anal. Calcd. for $C_{11}H_{15}FOSi$: C, 62.82; H, 7.19; Found: C, 62.97; H, 7.31.

Over a period of 2 hours, 9.74 g (0.094 mol) of trifluoromethyl hypofluorite was passed below the surface into a stirred solution of 16.82 g (0.08 mol) of 1-(4-fluorophenyl)vinyloxytrimethylsilane (from above) in 100 ml of chlorotrifluoromethane cooled to −70° C. to −78° C. The reaction mixture was warmed to room temperature and then distilled to give 8.74 g (70% yield) of α,4-difluoroacetophenone as a colorless liquid, bp 68°–75° C. (1.4 mm), that solidified on cooling to a white solid: mp 48°–50° C.; $^{19}F$ NMR (acetone-d6) δ−105.0 ppm (m, 1F), −232.0 ppm (d, J=47 Hz, 1F); $^1H$ NMR (acetone-d6) δ 5.69 ppm (d,J=47 Hz, 2H) and 7.1–8.2 ppm (m, 4H); ir (KBr) 6.27μ (C=O). Anal. Calcd. for $C_8H_6F_2O$: C, 61.54; H, 3.87; F, 24.34; Found: C, 61.97; H, 3.98; F, 24.29.

EXAMPLE 2

Fluorination of Ethyl Phenylacetate

Methyllithium in diethyl ether (0.25 mol, 140 ml of 1.8 M solution) was added dropwise to a solution of 27.6 g (0.27 mol) of diisopropylamine in 40 ml of diethyl ether. The reaction mixture was cooled to −78° C. and 26.3 g (0.16 mol) of ethyl phenylacetate were added dropwise. The reaction mixture was warmed to 0° C. and 46 ml (0.36 mol) of chlorotrimethylsilane were added rapidly. The reaction mixture was stirred overnight at 25° C., filtered to remove LiCl, and then distilled under reduced pressure to give 24.91 g (66% yield) of β-ethoxy-β-trimethylsiloxystyrene as a colorless liquid: bp 92° C. (0.7 mm); $^1H$ NMR (CFCl$_3$) δ 0.0 ppm (s, 9H), 0.94 ppm (t,J=7 Hz, 3H), 3.44 and 3.63 ppm (qs, J=7 Hz, 25:75, 2H), 4.17 and 4.36 ppm (ss, 25:75, 1H) and 6.57–7.20 ppm (m, 5H). Anal. Calcd. for $C_{13}H_{20}O_2Si$: C, 66.05; H, 8.53; Found: C, 66.26; H, 8.88.

A solution of 21.28 g (0.09 mol) of β-ethoxy-β-trimethylsiloxystyrene (from above) in 200 ml of $CFCl_3$ was cooled to −70° C. and 9.4 g (0.09 mol) of trifluoromethyl hypofluorite were passed into the solution over a period of 3 hours. The reaction mixture was warmed to room temperature and then distilled to give 12.52 g (77% yield) of ethyl α-fluorobenzeneacetate as a colorless liquid: bp 96°–98° C. (4.8 mm); $^{19}F$ NMR (CFCl$_3$) δ−180.1 ppm (d,J=48 Hz); $^1H$ NMR (CFCl$_3$) δ 1.10 ppm (t,J=7 Hz, 2H), 4.10 ppm (q,J=7 Hz, 2H), 5.66 ppm (d,J=48 Hz, 1H) and 7.1–7.6 ppm (m, 5H). Anal. Calcd. for $C_{10}H_{11}FO_2$: C, 65.92; H, 6.07; F, 10.43; Found: C, 66.09; H, 6.13; F, 10.33.

EXAMPLE 3

Fluorination of N,N-Dimethylbenzeneacetamide

Methyllithium in diethyl ether (140 ml of 1.8 M solution, 0.25 mol) was added dropwise to a solution of 27.6 g (0.27 mol) of diisopropylamine in 40 ml of dry diethyl ether. The reaction mixture was cooled to −70° C. and a solution of 26.1 g (0.16 mol) of N,N-dimethylbenzeneacetamide in 75 ml of diethyl ether was added dropwise. The reaction mixture was warmed to 0° C. and 46 ml (0.36 mol) of trimethylchlorosilane were added dropwise. The reaction mixture was stirred at 25° C. overnight, the solid was filtered off, and the filtrate was distilled to give 7.65 g of β-(N,N-dimethylamino)-β-trimethylsiloxystyrene as a light yellow oil: bp 75°–78° C. (0.5 mm); $^1H$ NMR (CDCl$_3$) δ 2.18 ppm (s, 6H), 4.83 ppm (s, 1H), 6.7–7.6 ppm (m, 5H) and 0.04 ppm (s, 9H). Anal. Calcd. for $C_{13}H_{21}NOSi$: C, 66.33; H, 8.99; N, 5.95; Found: C, 66.47; H, 9.11; N, 5.78.

A solution of 3.0 g (0.0127 mol) of β-(N,N-dimethylamino)-β-(trimethylsiloxy)styrene (from above) in 100 ml of chlorotrifluoromethane was cooled to −70° C. and 1.6 g (0.013 mol) of trifluoromethyl hypofluorite were passed into the solution over a period of 3 hours. The reaction mixture was warmed to room temperature and then distilled to give 1.49 g (65% yield) of α-fluoro-N,N-dimethylbenzeneacetamide as a colorless oil: bp 98°–100° C. (0.45 mm); $^{19}$F NMR (CCl$_3$F) δ −175.9 ppm (d,J=50 Hz); $^1$H NMR (CCl$_3$F) δ 2.86 ppm (s, 6H), 5.54 ppm (d,J=50 Hz, 1H) and 7.10–7.8 ppm (m, 5H). Anal. Calcd for C$_{10}$H$_{12}$FNO: C, 66.27; H, 6.68; F, 10.49; N, 7.73; Found: C, 66.41; H, 6.75; F, 10.30; N, 7.70.

EXAMPLE 4

Fluorination of Benzeneacetic Acid

A solution of butyllithium in hexane (0.4 mol, 250 ml of 1.6 M solution) was added to a solution of 40 g (0.4 mol) of diisopropylamine in 300 ml of tetrahydrofuran cooled in an ice-bath. A solution of 27.23 g (0.2 mol) of benzeneacetic acid in 200 ml of tetrahydrofuran was added near 0° C. and the reaction mixture was stirred for 30 minutes at 0° C. A 100 g portion of trimethylchlorosilane was added, the mixture was warmed to room temperature, stirred for 1.5 hours, and then filtered under nitrogen. The filtrate was evaporated to dryness under reduced pressure; the residue was dissolved in 80 ml of diethyl ether and filtered. The filtrate was evaporated to dryness and then distilled to give 37.2 g of β,β-[bis(trimethylsiloxy]styrene as a colorless liquid: bp 95° C. (0.5 mm).

A solution of 24.8 g (0.1 mol) of β,β-[bis-(trimethylsiloxy)]styrene (from above) in 300 ml of trichlorofluoromethane was cooled to −70° C. and 11.0 g (1.06 mol) of trifluoromethyl hypofluorite were passed into the solution. The reaction mixture was warmed to room temperature and then evaporated to dryness under reduced pressure. Water (5 ml) was added to the residue. An exothermic reaction ensued. Excess water was evaporated off at reduced pressure; the white residue was recrystallized from hexane to give 13.8 g (90% yield) of α-fluorobenzeneacetic acid as colorless crystals: mp 75°–77° C.; ir (KBr) 5.68μ (C=O); $^{19}$F NMR (CDCl$_3$) δ −181.4 ppm (d,J=48 Hz); $^1$H NMR (CDCl$_3$) δ 5.80 ppm (d,J=48 Hz, 1H), 7.43 ppm (5H) and 10.17 ppm (s, OH). Anal. Calcd. for C$_8$H$_7$FO$_2$: C, 62.34; H, 4.58; F, 12.33; Found: C, 62.14; H, 4.47; F, 12.39.

EXAMPLE 5

Fluorination of Phenylacetaldehyde

A mixture of 30.0 g (0.25 mol) of phenylacetaldehyde, 32.6 g (0.3 mol) of trimethylchlorosilane, 60.6 g (0.6 mol) of triethylamine, and 100 ml of N,N-dimethylformamide was refluxed overnight, cooled and diluted with 200 ml of pentane. The mixture was washed successively with cold 5% aqueous sodium bicarbonate, 1.5 N hydrochloric acid, and 5% aqueous sodium bicarbonate, dried (over MgSO$_4$), and then distilled to give 21.15 g of α-trimethylsiloxystyrene as a colorless liquid: bp 80°–83.5° C. (3.8 mm); $^1$H NMR (CDCl$_3$) δ 0.07 ppm (s, 9H), 5.87 ppm (d,J=12 Hz, 1H), 6.80 ppm (d,J=12 Hz, 1H) and 7.03 ppm (m, 5H).

A solution of 17.3 g (0.09 mol) of α-trimethylsiloxystyrene (from above) in 250 ml of trichlorofluoromethane was cooled to −70° C. and 9.9 g (0.095 mol) of trifluoromethyl hypofluorite were passed into the solution over a 2 hour period. The reaction mixture was warmed to 25° C. and then distilled under reduced pressure to give 8.7 (70% yield) of α-fluorophenylacetaldehyde as a colorless liquid: bp 35°–36° C. (1.0 mm); $^{19}$F NMR (CDCl$_3$) δ −178.8 ppm (d,d,J=49, 24 Hz). This sample polymerized to a viscous liquid on standing at 25° C. overnight; $^{19}$F NMR of polymer (CDCl$_3$) δ −193.7 ppm (m). Anal. (of polymer) Calcd. for (C$_8$H$_7$FO)$_n$: C, 69.55; H, 5.11; F, 13.75; Found: C, 69.85; H, 5.33; F, 13.43.

EXAMPLE 6

When the general process of Example 1 was repeated, except that cyclohexanone was used as the ketone, 2-fluorocyclohexanone, bp 46° C. (2.8 mm), was obtained. Anal. Calcd. for C$_6$H$_9$FO: F, 16.36; Found: F, 16.21.

EXAMPLE 7

Fluorination of Norcamphor

Methyllithium in diethyl ether (141 ml of 1.8 M solution) was added dropwise to a solution of 27.6 g of diisopropylamine in 38 ml of dry diethyl ether. The resulting solution was cooled to −78° C. and 19.7 g of norcamphor in 20 ml of diethyl ether were added dropwise. The reaction mixture was warmed to 0° C. and 46 ml of chlorotrimethylsilane were added. The reaction mixture was warmed to 25° C., stirred for 30 minutes, extracted with cold 5% aqueous sodium bicarbonate, dried (over MgSO$_4$) and then distilled to give 22.3 g of 2-trimethylsiloxybicyclo[2.2.1]-hept-2-ene as a colorless liquid: bp 70°–73° C. (14 mm).

A solution of 16.4 g (0.09 mol) of the aforesaid 2-trimethylsiloxybicyclo[2.2.1]-hept-2-ene in 100 ml of CFCl$_3$ was cooled to −70° to −78° C. and 9.4 g (0.09 mol) of trifluoromethyl hypofluorite were passed into the solution over a period of 3 hours. The reaction mixture was warmed to room temperature and then distilled to give 12.68 g of a colorless liquid: bp 79°–80° C. (17 mm). A 10.18 g sample of this product was heated to 150°–160° C. and held at this temperature until gassing stopped. The sample solidified on cooling to give 7.69 g (83% yield from the enol ether) of exo-3-fluoronorcamphor as a white, waxy solid: mp 99°–101° C.; $^{19}$F NMR (CFCl$_3$) δ −190.0 ppm (J$_{FH}$=53 Hz); $^1$H NMR (CFCl$_3$) δ 1.2–2.9 ppm (m, 6H), 4.11 ppm (d,d,J=53, 2 Hz, 1H). Anal. Calcd. for C$_7$H$_9$FO: C, 65.61; H, 7.08; F, 14.83; Found: C, 65.91; H, 7.12; F, 14.71.

When camphor is used in the above process, the corresponding siloxy derivative which is formed, upon reaction with trifluoromethyl hypofluorite, gives α-fluorocamphor.

EXAMPLE 8

Fluorination of Deoxybenzoin

A mixture of 32.6 g (0.3 mol) of trimethylchlorosilane, 39.25 g (0.2 mol) of deoxybenzene and 100 ml of N,N-dimethylformamide was refluxed overnight, then cooled and mixed with 200 ml of pentane. The reaction mixture was washed three times with 300 ml of cold 5% aqueous sodium bicarbonate, with 1.5 M hydrochloric acid and then with the bicarbonate again, after which it was dried (over MgSO$_4$) and distilled to give 44.05 g (82% yield) of α-trimethylsiloxystilbene as a colorless liquid: bp 122°–127° C. (0.5 mm); ir (liquid) 6.13μ (C=C); $^1$H NMR (CDCl$_3$) δ 0.0 ppm (s, 9H), 6.1 ppm (s, 1H) and 7.0–7.8 ppm (m, 5H). Anal. Calcd. for C$_{17}$H$_{20}$OSi: C, 76.07; H, 7.51; Found: C, 76.67; H, 7.90.

A solution of 18.8 g (0.07 mol) of the aforesaid α-trimethylsiloxystilbene in 200 ml of chlorotrifluoromethane was cooled to −70° C. and 7.3 g (0.07 mol) of trifluoromethyl hypofluorite were passed into the solution over a 3 hour period. The reaction mixture then was warmed to room temperature and evaporated to dryness under reduced pressure to give a white solid. Recrystallization from heptane gave 10.81 g (72% yield) of α-fluoro-α-phenylacetophenone as colorless crystals: mp 50°–51° C.; $^{19}$F NMR (CDCl$_3$) δ −176.5 ppm (d, J=49 Hz); $^1$H NMR (CDCl$_3$) δ 6.52 ppm (d, J=49 Hz, 1H), 7.2–8.2 ppm (m, 10H). Anal. Calcd. for C$_{14}$H$_{11}$FO: C, 78.49; H, 5.18; F, 8.87; Found: C, 78.52; H, 5.13; F, 8.65.

EXAMPLE 9

Fluorination of Ethyl 4-Isobutyl-α-methylphenylacetate

Methyllithium in diethyl ether (0.25 mol, 140 ml of 1.8 M solution) was added dropwise to a solution of 27.6 g (0.27 mol) of diisopropylamine in 40 ml of diethyl ether. The reaction mixture was cooled to −70° C. and 37.5 g (0.16 mol) of ethyl 4-isobutyl-α-methylphenylacetate were added dropwise. The reaction mixture was warmed to 0° C. and 46 ml (0.36 mol) of chlorotrimethylsilane were added. The reaction mixture was stirred overnight at 25° C., filtered and then distilled to give 34.3 g (70% yield) of β-ethoxy-4-isobutyl-α-methyl-β-(trimethylsiloxy)-styrene as a colorless liquid, bp 129°–130° C. (0.4 mm). Anal. Calcd. for C$_{18}$H$_{30}$O$_2$Si: C, 70.53; H, 9.87; Found: C, 70.38; H, 9.78.

A solution of 27.59 g (0.09 mol) of β-ethoxy-4-isobutyl-α-methyl-β-(trimethylsiloxy)styrene in 250 ml of CFCl$_3$ was cooled to −70° C. and 9.4 g (0.09 mol) of trifluoromethyl hypofluorite were passed into the solution over a period of 4 hours. The reaction mixture then was warmed to room temperature and distilled to give 19.3 g (85% yield) of ethyl α-fluoro-4-isobutyl-α-methylphenylacetate as a colorless liquid; bp 88°–89° C. (0.4 mm); $^{19}$F NMR (CDCl$_3$) δ 150.9 ppm (q, J=22.5 Hz); $^1$H NMR (CDCl$_3$) α 0.91 ppm (d, J=6 Hz, 6H), 1.22 ppm (t, J=7 Hz, 3H), 1.88 ppm (m, 1H), 1.91 ppm (d, J=22.5 Hz, 3H), 2.48 ppm (d, J=6 Hz, 2H), 4.21 ppm (q, J=7 Hz, 2H) and 7.0–7.6 ppm (m, 4H). Anal. Calcd. for C$_{15}$H$_{21}$FO$_2$: C, 71.40; H, 8.39; F, 7.53; Found: C, 71.63; H, 8.35; F, 7.43.

EXAMPLE 10

A. Fluorination of 7-Chloro-1,3-dihydro-1-methyl-5-phenyl-2H-1,4-benzodiazepin-2-one A solution of methyllithium in diethyl ether (0.0275 mol, 15.3 ml of 1.8 M solution) was added dropwise to a solution of 3.04 g (0.03 mol) of diisopropylamine in 25 ml of diethyl ether. The reaction mixture was cooled to −70° C. and a solution of 7.12 g (0.025 mol) of 7-chloro-1,3-dihydro-1-methyl-5-phenyl-2H-1,4-benzodiazepin-2-one in 40 ml of tetrahydrofuran was added dropwise. The reaction mixture became dark red. Trimethylchlorosilane (11.4 ml; 0.09 mol) was added dropwise, after which the reaction mixture was warmed to room temperature, stirred for 3 hours and then filtered. The filtrate was evaporated to dryness and the residue was dissolved in 150 ml of trichlorofluoromethane. This solution was filtered to remove undissolved solid; the filtrate was evaporated to dryness under reduced pressure to give 8.52 g of 7-chloro-1-methyl-5-phenyl-2-trimethylsiloxy-1H-1,4-benzodiazepine as a light orange glass: $^1$H NMR (CCl$_3$F) δ 0.0 ppm (s, 9H), 2.62 ppm (s, 3H), 5.76 ppm (s, 1H) and 6.4–7.6 ppm (m, 8H).

A solution of 8.52 g of the aforesaid 7-chloro-1-methyl-5-phenyl-2-trimethylsiloxy-1H-1,4-benzodiazepine in 150 ml of trichlorofluoromethane was cooled to −70° C. and 2.4 g of trifluoromethyl hypofluorite were passed into the solution over a period of 3 hours. The reaction mixture then was warmed to room temperature and evaporated to dryness under reduced pressure to give 7.60 g of crude 7-chloro-3-fluoro-1,3-dihydro-1-methyl-5-phenyl-2H-1,4-benzodiazepin-2-one as a light tan powder: mp 130°–140° C.; $^{19}$F NMR (CCl$_3$D) δ−161.7 ppm (d,J=57 Hz).

B. Fluorination of 7-Trifluoromethyl-1,3-dihydro-1-methyl-5-phenyl-2H-1,4-benzodiazepin-2-one Following the general procedure of Part A, 2.4 g of 7-trifluoromethyl-1,3-dihydro-1-methyl-5-phenyl-2H-1,4-benzodiazepin-2-one was reacted with trimethylchlorosilane. The filtrate was evaporated, the residue was dissolved in CFCl$_3$ and the CFCl$_3$ was removed by evaporation to give 7-trifluoromethyl-1-methyl-5-phenyl-2-trimethylsiloxy-1H-1,4-benzodiazepin which was again dissolved in CFCl$_3$ and reacted with trifluoromethyl hypofluorite to give 7-trifluoromethyl-3-fluoro-1,3-dihydro-1-methyl-5-phenyl-2H-1,4-benzodiazepin-2-one whose measured mass spectrum was m/c 336.0859; Calculated for C$_{17}$H$_{12}$ON$_2$F$_4$: 336.0885.

EXAMPLE 11

Fluorination of 2,4-Dichlorophenoxyacetic Acid

A solution of butyllithium in hexane (62.5 ml of 1.6 M solution, 0.1 mol) was added dropwise to a solution of 11.0 g (0.11 mol) of diisopropylamine in 100 ml of tetrahydrofuran at 25° C. The reaction mixture was cooled to 0° C. and a solution of 11.05 g (0.05 mol) of 2,4-dichlorophenoxyacetic acid in 100 ml of tetrahydrofuran was added dropwise. The reaction mixture was stirred for 1 hour at 0° C. and then 28 ml (0.27 mol) of trimethylchlorosilane were added. The mixture then was warmed to room temperature, stirred overnight and then filtered. The filtrate was evaporated under reduced pressure and the residue was dissolved in 100 ml of trichlorofluoromethane. The solution was filtered and the filtrate was evaporated to give 18.3 g of a viscous colorless oil. The oil was dissolved in 200 ml of trichlorofluoromethane and the resulting solution was cooled to −70° C. Trifluoromethyl hypofluorite (5.2 g, 0.05 mol) was passed into the solution over a 2 hour period; the reaction mixture then was warmed to room temperature and evaporated under reduced pressure. The residue oil was dissolved in 200 ml of trichlorofluoromethane, shaken with 10 ml of water and the organic layer was evaporated under reduced pressure to give a solid residue. Recrystallization of the residue from chlorobutane gave 8.36 g (70% yield) of 2,4-dichlorophenoxyfluoroacetic acid: mp 89°–91° C.; $^1$H NMR (CDCl$_3$) δ 5.92 ppm (d, J=59 Hz); 7.1–7.5 ppm (m, 3H) and 8.55 ppm (s, OH); $^{19}$F NMR(CDCl$_3$) δ−131.5 ppm (d, J=59 Hz); ir (KBr) 5.65μ (C=O). Anal. Calcd. for C$_8$H$_5$Cl$_2$FO$_3$: C, 40.20; H, 2.11; Cl, 29.67; F, 7.95; Found: C, 39.85; H, 2.40; Cl, 29.37; F, 7.77.

EXAMPLE 12

Fluorination of 2,4,5-Trichlorophenoxyacetic Acid

A solution of butyllithium in hexane (125 ml of 1.6 M solution, 0.2 mol) was added dropwise to a solution of 22.0 g (0.22 mol) of diisopropylamine in 100 ml of tetrahydrofuran at 25° C. The reaction mixture was cooled to 0° C. and a solution of 25.55 g (0.1 mol) of 2,4,5-trichlorophenoxyacetic acid in 200 ml of tetrahydrofuran was added dropwise. The reaction mixture was stirred for 1 hour at 0° C. and then 56 ml (0.44 mol) of trimethylchlorosilane were added. The mixture was warmed to room temperature, stirred overnight and then filtered. The filtrate was evaporated under reduced pressure and the residue was dissolved in 200 ml of trichlorofluoromethane. The solution was filtered and the filtrate was evaporated to give 40.0 g of a viscous colorless oil. The oil was dissolved in 400 ml of trichlorofluoromethane and the resulting solution was cooled to −70° C. Trifluoromethyl hypofluorite (10.4 g, 0.1 mol) was passed into the solution over a 3 hour period; the reaction mixture then was warmed to room temperature and evaporated under reduced pressure. The residual oil was dissolved in 400 ml of trichlorofluoromethane, shaken with 20 ml of water and the organic layer was evaporated under reduced pressure. The resultant residue was recrystallized from toluene-hexane to give 20.8 g (76% yield) of 2,4,5-trichlorophenoxyfluoroacetic acid as a colorless crystalline powder: mp 104°-132° C. (dec.); $^1$H NMR (DMSO-d$_6$) δ6.37 ppm (d, J=59 Hz, 1H), 7.70 ppm (s, 1H), 7.90 ppm (s, 1H) and 9.6 ppm (OH); $^{19}$F NMR (DMSO-d$_6$) δ−132.9 ppm (d, J=59 Hz). Anal. Calcd. for C$_8$H$_4$Cl$_3$FO$_3$: C, 35.14; H, 1.47; Cl, 38.89; F, 6.95 Found: C, 34.50; H, 1.52; Cl, 37.30; F, 6.95.

EXAMPLE 13

Fluorination of 2-Naphthoxyacetic Acid

A solution of butyllithium in hexane (62.5 ml of 1.6 M solution, 0.1 mol) was added dropwise to a solution of 11.0 g (0.11 mol) of diisopropylamine in 100 ml of tetrahydrofuran at 25° C. The reaction mixture was cooled to 0° C. and a solution of 10.1 g (0.05 mol) of 2-naphthoxyacetic acid in 100 ml of tetrahydrofuran was added dropwise. The reaction mixture was stirred for 1 hour at 0° C. and then 28 ml (0.22 mol) of trimethylchlorosilane were added. The reaction mixture was stirred for 18 hours at room temperature and the precipitated solid was filtered off. The filtrate was evaporated to dryness under reduced pressure; the resultant residue was dissolved in 100 ml of CFCl$_3$ and the solution was filtered. The filtrate was evaporated to dryness to give 15.4 g of a viscous syrup which was dissolved in 200 ml of CFCl$_3$. The solution was cooled to −70° C. and 5.2 g (0.05 mol) of trifluoromethyl hypofluorite were passed into the solution over a period of 50 minutes. The reaction mixture was warmed to room temperature and evaporated to dryness under reduced pressure. The resultant syrupy residue was suspended in 100 ml of water and stirred overnight. The solid that formed was suspended in 100 ml of water; the suspension was stirred overnight and then filtered. The solid that was collected on the filter was washed with water and dried in vacuum over P$_2$O$_5$ to give 7.71 g (70% yield) of 2-fluoro-2-(2-naphthoxy)acetic acid as a white crystalline powder: mp >100° C. (dec.); $^1$H NMR (DMSO-d$_6$) δ6.35 ppm (d, J=60 Hz, 1H), 7.1-8.3 ppm (m, 7H), $^{19}$F NMR (DMSO-d$_6$) δ−130.7 ppm (d, J=60 Hz). Anal. Calcd. for C$_{12}$H$_9$FO$_3$: C, 65.45; H, 4.12; F, 8.63; Found: C, 65.31; H, 3.98, F, 8.73.

EXAMPLE 14

Fluorination of 4-(2-Methylpropyl)benzeneacetic Acid

Butyllithium in hexane (175 ml of 1.6 M solution, 0.28 mol) was added to a solution of 30 g (0.3 mol) of diisopropylamine in 200 ml of tetrahydrofuran at 25° C. The reaction mixture was cooled to 0° C. and a solution of 26.0 g (0.135 mol) of 4-(2-methylpropyl)benzeneacetic acid in 200 ml of tetrahydrofuran was added dropwise near 0° C. The mixture was stirred for 1 hour at 0° C. and then 70 ml (0.55 mol) of trimethylchlorosilane were added. The reaction mixture was warmed to room temperature and stirred for 2 hours. The solid that formed was filtered off; the filtrate was concentrated under reduced pressure and then mixed with 100 ml of diethyl ether. The resultant mixture was filtered and the filtrate was concentrated. Distillation of the residue gave 31.92 g (70% yield) of 4-(2-methylpropyl)-β,β-bis(trimethylsiloxy)styrene as a colorless liquid: bp 128°-130° C. (0.4 mm); ir (liquid) 6.07μ (C=C). Anal. Calcd. for C$_{18}$H$_{32}$O$_2$Si$_2$: C, 64.22; H, 9.58; Found: C, 64.34; H, 9.95.

A solution of 16.8 g (0.05 mol) of the aforesaid 4-(2-methylpropyl)-β,β-bis(trimethylsiloxy)-styrene in 250 ml of CFCl$_3$ was cooled to −70° C. and 5.2 g (0.05 mol) of trifluoromethyl hypofluorite were passed into the solution over a period of 1 hour. The reaction mixture was warmed to room temperature (25° C.) and then evaporated under reduced pressure to give 14.1 g (100% yield) of crude trifluoromethylsilyl α-fluoro-4-(2-methylpropyl)benzeneacetate as a colorless oil: $^{19}$F NMR (CFCl$_3$) δ−176.8 ppm (d, J=49 Hz); $^1$H NMR (CFCl$_3$, ext. TMS) δ 0.01 ppm (s, 9H), 0.66 ppm (d, J=6 Hz, 6H), 1.55 ppm (m, 1H), 2.22 ppm (d, J=6 Hz, 2H), 5.30 ppm (d, J=49 Hz, 1H) and 6.7-7.2 ppm (A$_2$B$_2$).

Water, 5 ml, was added to the oil and the mixture was stirred vigorously for 30 minutes, at which time it solidified. The volatiles were removed by evaporation at reduced pressure to give 10.5 g (100% yield) of crude product. Recrystallization from pentane gave 6.0 g of α-fluoro-4-(2-methylpropyl)-benzeneacetic acid as colorless crystals: mp 64°-66° C.; $^{19}$F NMR (CDCl$_3$) δ−179.9 ppm (d, J=48 Hz); $^1$H NMR (CDCL$_3$) δ 0.88 ppm (d, J=6 Hz, 6H), 1.87 ppm (m, 1H), 2.49 ppm (d, J=5 Hz, 2H), 5.78 ppm (d, J=48 Hz, 1H) and 7.0-7.6 ppm (A$_2$B$_2$). Anal. Calcd. for C$_{12}$H$_{15}$FO$_2$: C, 68.55; H, 7.19; Found: C, 68.28; H, 7.26.

EXAMPLE 15

Fluorination of Phenoxyacetic Acid

A solution of butyllithium in hexane (250 ml of 1.6 M solution, 0.4 mol) was added to a solution of 40 g (0.4 mol) of diisopropylamine in 300 ml of tetrahydrofuran cooled in an ice bath. A solution of 30.43 g (0.2 mol) of phenoxyacetic acid in 200 ml of tetrahydrofuran was added at 0° C. and the reaction mixture was stirred for 30 minutes at 0° C. Chlorotrimethylsilane (100 g) was added; the mixture was warmed to room temperature and stirred for 2 hours and then filtered under nitrogen. The filtrate was concentrated under reduced pressure and then mixed with 80 ml of diethyl ether; the mixture was filtered. Distillation of the filtrate gave 41.6 g (70% yield) of bis(trimethylsilyl)phenoxyketene acetal as a colorless liquid: bp 80°-82° C. (1.0 mm).

A solution of 41.5 g (0.14 mol) of the aforesaid bis(-trimethylsilyl)phenoxyketene acetal in 450 ml of chlorotrifluoromethane was cooled to −70° C. and 15.0 g (0.144 mol) of CF$_3$OF were passed into the solution over a 3 hour period. The reaction mixture was warmed to room temperature and then evaporated at reduced pressure. The liquid residue was mixed with 10 ml of water and stirred vigorously. The semisolid mixture was dried under reduced pressure and then recrystallized from heptane to give 16.65 g (70% yield) of α-fluoro-α-phenoxyacetic acid as white crystals: mp 61°–63° C.; $^{19}$F NMR (CDCl$_3$) δ−130.1 ppm (d, J=59 Hz); $^1$H NMR (CDCl$_3$) δ6.00 ppm (d, J=59 Hz, 1H), 6.9–7.6 ppm (m, 5H) and 10.4 ppm (s, 1H); ir (KBr) 5.70μ (C=C). Anal. Calcd. for C$_8$H$_7$FO$_3$: C, 56.47; H, 4.15; F, 11.17; Found: C, 56.39; H, 4.05; F, 10.95.

EXAMPLE 16

Fluorination of 2-(p-Chlorophenyl)acetic Acid

A cooled (0°–5° C.) solution of 41.4 g (0.41 mol) of diisopropylamine in 300 ml of tetrahydrofuran was treated slowly with butyllithium in hexane (250 ml of a 1.6 M solution, 0.4 mol). A solution of 34.12 g (0.2 mol) of p-chlorophenylacetic acid in 200 ml of tetrahydrofuran was added dropwise and the reaction mixture was stirred 30 minutes at 0° C. Trimethylchlorosilane (100 g) was added and the mixture was allowed to warm to room temperature and was stirred for 1.5 hours. The contents of the flask were filtered under nitrogen and the filtrate was evaporated under reduced pressure. The residue was dissolved in 80 ml of diethyl ether; the solution was filtered and the filtrate was evaporated. The resultant residue was distilled in a Vigreux column, maintaining the pot temperature below 130° C. to prevent decomposition of the product. The product β,β-bis(trimethylsiloxy)p-chlorostyrene, 32.56 g (52% yield), was obtained as a colorless liquid, bp 110° C. (0.1 mm); $^1$H NMR (CDCl$_3$) δ7.0–7.4 (m, 4H), δ4.52 (s, 1H); δ0.22 (s) and δ0.26 (s) together 18H. The moisture sensitive product was stored under nitrogen.

A solution of 29.92 g (0.095 mol) of the aforesaid β,β-bis(trimethylsiloxy)p-chlorostyrene in 300 ml of CFCl$_3$ was cooled to −70° C. and 9.88 g (0.095 mol) of trifluoromethyl hypofluorite were passed into the solution over a period of 2 hours. The mixture was allowed to warm to room temperature and evaporated to dryness under reduced pressure. The resultant white solid residue was stirred with 10 ml of water for approximately 10 minutes. The solids were recrystallized from 1 l of hexane to give 9.38 g (53% yield) of p-chlorophenylfluoroacetic acid as shiny white crystals, mp 66°–68° C.; $^1$H NMR (CDCl$_3$) δ5.75 (d, J≅47 Hz, 1H), δ7.35 ppm (s, 4H), δ10.95 (s, 1H); $^{19}$F NMR (CDCl$_3$) δ−182.60 (d, J≅47 Hz).

By the above general procedure cyclopentanone gives 2-fluorocyclopentanone; acetophenone give α-fluoroacetophenone; 3,3-dimethylbutan-2-one gives 1-fluoro-3,3-dimethylbutan-2-one; and 4-tert-butylcyclohexanone gives 2-fluoro-4-tert-butylcyclohexanone.

Using the general procedure of Examples 2 and 3, except that 3-phenyl-2-propanone, 2-heptanone, butyraldehyde, 2-butanone, 1-decalone and 2-methoxycyclohexanone are used as the ketone, 3-fluoro-3-phenyl-2-propanone, 1-fluoro-2-heptanone, α-fluorobutyraldehyde, 1-fluorobutan-2-one, 2-fluoro-1-decalone and 6-fluoro-2-methoxycyclohexanone, respectively, are obtained. The siloxy derivatives of the aforesaid ketones are described by House et al., loc. cit.

The general procedure of this invention is especially useful for the preparation of fluoroketosteroids; for example, estrone, testosterone and androsterone can be reacted with trimethylchlorosilane to give the 3,17-bis-trimethylsiloxy derivates which, upon reaction with trifluoromethyl hypofluorite, give 16-fluoroestrone, 2-fluorotestosterone and 16-fluoroandrosterone, respectively. These compounds have utility in hormonal applications.

Similarly, 2-acetylthiophene, 5-nonanone and stearone give, for example, by treatment with chlorotriethylsilane, the corresponding siloxy compounds which, upon reaction with trifluoromethyl hypofluorite, give 2-β-fluoroacetylthiophene, 4-fluorononane-5-one and α-fluorostearone, respectively.

As a further example,

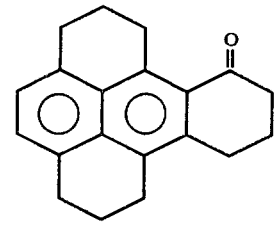

is converted, through its siloxy derivative to,

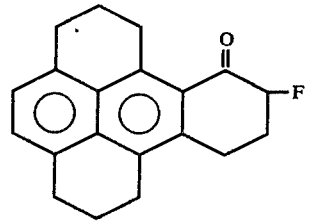

by means of the process of this invention. Other carbonyl compounds that can be employed in the above general procedures to give the α-fluoro compounds from the enol siloxanes include cyclopropyl methyl ketone, cyclohexyl methyl ketone, 4-methoxyacetophenone and 4-chlorobutan-2-one.

Lactones such as γ-butyrolactone and δ-valerolactone give the corresponding siloxy compounds which are converted to the α-fluorobutyrolactone and α-fluorovalerolactone using trifluoromethyl hypofluorite.

Esters such as diethylmalonate, phenyl palmitate, dimethyl sebacate, ethyl 1-methyl-3-indole acetate are converted to the corresponding monosiloxy compounds which, upon reaction with trifluoromethyl hypofluorite, are converted to diethyl α-fluoromalonate, phenyl α-fluoropalmitate, dimethyl α-fluorosebacate and ethyl 1-methyl-3-α-fluoroacetate, respectively.

Other acids that can be used in Example 4 in place of benzeneacetic acid include 7-methoxy-2-α-methylnaphthaleneacetic acid (naproxen), 2-thienylacetic acid, 2-pyridylacetic acid, m-chlorophenylacetic acid and oleic acid. These give 7-methoxy-2-α-methylfluoronaphthaleneacetic acid, 2-α-fluorothienylacetic acid, 2-α-fluoropyridylacetic acid, m-chlorophenyl-α-fluoroacetic acid and α-fluorooleic acid, respectively, by treatment of their bis-siloxyhydrocarbyl derivatives with, for example, trifluoromethyl hypofluorite.

When 7-trifluoromethyl-1,3-dihydro-1-methyl-5-phenyl-2H-1,4-benzodiazepin-2-one was reacted by the procedure set forth in Example 10B, 7-trifluoromethyl-3-fluoro-1,3-dihydro-1-methyl-5-phenyl-2H-1,4-benzodiazepin-2-one was obtained. Likewise, N-methylcaprolactam is converted, through its siloxy derivative, to N-methyl-α-fluorocaprolactam.

BEST MODE FOR CARRYING OUT THE INVENTION

The best mode presently contemplated for carrying out this invention involves the use of $CF_3OF$ in $CFCl_3$ solvent at $-80°$ to $-60°$ C. with an equimolar amount of a trihydrocarbylsilyl enol ether of a carbonyl compound such as 7-chloro-1-methyl-5-phenyl-2-trimethylsiloxy-1H-1,4-benzodiazepine or β,β-[bis(trimethylsiloxy)] styrene.

INDUSTRIAL APPLICABILITY

Many of the α-fluorocompounds obtained by the process of this invention are known and have applications as described in the chemical literature. Generally, they are of value in applications where the non-fluorinated compounds have found use. For example, the compounds of Examples 11 and 12 are herbicides. The compound of Example 7 is particularly useful as a tranquilizer and muscle relaxant as shown in U.S. Pat. No. 4,120,856. The process makes readily attainable many α-fluorocarbonyl compounds whose synthesis by prior methods is generally difficult.

It is claimed:

1. Process for preparing an organic compound of the formula $R^2R^2CFC(O)R^3$, which process comprises contacting and reacting in a reaction mixture which includes an inert solvent, at a temperature of $-40°$ C. to $-100°$ C., ROF and $$R^2R^2C=C\begin{matrix}OSi(R^1)_3\\R^3\end{matrix}$$

R is polyfluoroperhaloalkyl of 1-6 carbon atoms or $FOCF_2$;

$R^1$ is hydrocarbyl of 1-6 carbon atoms;

each $R^2$ is selected from H, alkyl of 1-17 carbon atoms, cycloalkyl of 3-6 carbon atoms, aryl, heteroaryl and such alkyl, cycloalkyl, aryl and heteroaryl substituted by halogen or alkoxy of 1-6 carbon atoms;

$R^3$ is selected from H, alkyl and haloalkyl of 1-16 carbon atoms, cycloalkyl of 3-10 carbon atoms, aryl and haloaryl, $OSi(R^1)_3$, OH, $NH_2$, alkoxy of 1-6 carbon atoms, aryloxy, $NHR^1$ and $NR^1_2$ wherein $R^1$ is alkyl of 1-6 carbon atoms, N-arylamino and nitrogen or sulfur heterocyclic of 4-5 carbon atoms;

$R^3$ and one $R^2$ taken together is a diradical which with the C=C group is carbocyclic, heterocyclic or haloheterocyclic, and recovering from the reaction mixture the compound of the formula $R^2R^2CFC(O)R^3$.

2. Process of claim 1 wherein R is $CF_3$ and $R^1$ is $CH_3$.

3. Process of claim 1 wherein the compound of the formula $R^2R^2CFC(O)R^3$ is a ketone.

4. Process of claim 1 wherein the compound of the formula $R^2R^2CFC(O)R^3$ is an amide.

5. Process of claim 4 wherein the compound of the formula $R^2R^2CFC(O)R^3$ is 7-chloro-3-fluoro-1,3-dihydro-1-methyl-5-phenyl-2H-1,4-benzodiazepin-2-one.

6. Process of claim 4 wherein the compound of the formula $R^2R^2CFC(O)R^3$ is 7-trifluoromethyl-3-fluoro-1,3-dihydro-1-methyl-5-phenyl-2H-1,4-benzodiazepin-2-one.

7. Process of claim 1 wherein the compound of the formula $R^2R^2CFC(O)R^3$ is an aldehyde.

8. Process of claim 1 wherein the compound of the formula $R^2R^2CFC(O)R^3$ is an ester.

9. Process of claim 1 wherein the compound of the formula $R^2R^2CFC(O)R^3$ is an acid.

10. Process of claim 9 wherein the acid is 2,4-dichlorophenoxyfluoroacetic acid.

11. Process of claim 9 wherein the acid is 2,4,5-trichlorophenoxyfluoroacetic acid.

12. Process of claim 9 wherein the acid is p-chlorophenylfluoroacetic acid.

13. Process of claim 9 wherein the acid is α-fluorobenzeneacetic acid.

14. Process of claim 1 wherein the aryl, heteroaryl, haloaryl, aryloxy and N-arylamino groups are of 6-10 carbon atoms and the carbocyclic, halocarbocyclic, heterocyclic, except the nitrogen or sulfur heterocyclic $R^3$, and haloheterocyclic are of 5-16 carbon atoms.

* * * * *